(12) United States Patent
Beach et al.

(10) Patent No.: US 10,274,571 B2
(45) Date of Patent: Apr. 30, 2019

(54) METHOD AND APPARATUS FOR MEASURING EXCHANGE STIFFNESS AT A PATTERNED DEVICE LEVEL

(71) Applicant: Samsung Electronics Co., LTD., Gyeonggi-do (KR)

(72) Inventors: Robert Beach, Los Gatos, CA (US); Dmytro Apalkov, San Jose, CA (US); Volodymyr Voznyuk, Fremont, CA (US); Ilya Krivorotov, San Jose, CA (US); Chengcen Sha, San Jose, CA (US)

(73) Assignee: Samsung Electronics Co., Ltd., Gyeonggi-do (KR)

(*) Notice: Subject to any disclaimer, the term of this patent is extended or adjusted under 35 U.S.C. 154(b) by 0 days.

(21) Appl. No.: 15/478,226

(22) Filed: Apr. 3, 2017

(65) Prior Publication Data

US 2018/0205001 A1 Jul. 19, 2018

Related U.S. Application Data

(60) Provisional application No. 62/447,525, filed on Jan. 18, 2017.

(51) Int. Cl.
*G01R 33/60* (2006.01)
*H01L 27/22* (2006.01)
(Continued)

(52) U.S. Cl.
CPC ............ *G01R 33/60* (2013.01); *G01N 24/10* (2013.01); *G11C 11/02* (2013.01); *G11C 29/021* (2013.01); *G11C 29/028* (2013.01); *G11C 29/24* (2013.01); *G11C 29/50008* (2013.01); *H01L 43/08* (2013.01); *H01L 43/12* (2013.01);
(Continued)

(58) Field of Classification Search
CPC ....... H01L 27/22; H01L 27/222; H01L 43/02; H01L 43/08; H01L 43/12; G01R 33/60
See application file for complete search history.

(56) References Cited

U.S. PATENT DOCUMENTS 6,713,195 B2 3/2004 Wang
8,134,864 B2 3/2012 Victora
(Continued)

OTHER PUBLICATIONS

"Spin Torque Driven Magnetization Dynamics in Nanoscale Magnetic Tunnel Junctions" (Year: 2016).*
(Continued)

*Primary Examiner* — Fazli Erdem
(74) *Attorney, Agent, or Firm* — Van Pelt, Yi & James LLP

(57) ABSTRACT

A method and apparatus determine an exchange stiffness of a free layer residing in a magnetic junction. The method includes performing spin torque ferromagnetic resonance (ST-FMR) measurements for the magnetic junction. The ST-FMR measurements indicate characteristic frequencies corresponding to spin wave modes in the free layer. The method also includes calculating the exchange stiffness of the free layer based upon the plurality of characteristic frequencies. In some embodiments, the magnetic junction resides on a wafer including other magnetic junctions for a device. The magnetic junctions may be arranged as a magnetic memory. The magnetic junction undergoing ST-FMR has a different aspect ratio than the magnetic junctions.

10 Claims, 5 Drawing Sheets

(51) Int. Cl.
 *H01L 43/08* (2006.01)
 *G11C 11/02* (2006.01)
 *H01L 43/12* (2006.01)
 *G01N 24/10* (2006.01)
 *G11C 29/02* (2006.01)
 *G11C 29/24* (2006.01)
 *G11C 29/50* (2006.01)
 *G11C 11/16* (2006.01)

(52) U.S. Cl.
 CPC .. *G11C 11/1675* (2013.01); *G11C 2029/5006* (2013.01); *H01L 27/222* (2013.01)

(56) References Cited

U.S. PATENT DOCUMENTS

| | | | |
|---|---|---|---|
| 8,456,962 | B2 | 6/2013 | Yamane |
| 8,981,506 | B1 | 3/2015 | Zhou |
| 2007/0096229 | A1 | 5/2007 | Yoshikawa |
| 2007/0259209 | A1* | 11/2007 | Slavin .................. B82Y 25/00 428/692.1 |
| 2010/0033881 | A1* | 2/2010 | Carey .................. B82Y 10/00 360/324.11 |
| 2012/0242438 | A1* | 9/2012 | Morise ................ H01F 10/3295 335/302 |
| 2012/0326712 | A1* | 12/2012 | Tudosa ................ G01R 33/093 324/252 |
| 2016/0125924 | A1* | 5/2016 | Kita ...................... G11C 11/161 365/158 |
| 2016/0169988 | A1 | 6/2016 | Sirringhaus |

OTHER PUBLICATIONS

"Exchange Stiffness in Ultrathin Perpendicularly-Magnetized CoFeB Layers Determined Using Spin Wave Spectroscopy" (Year: 2016).*

"Material Parameters of Perpendicularly Magnetized Tunnel Junctions from Spin Torque Ferromagnetic Resonance Techniques" (Year: 2016).*

* cited by examiner

METHOD AND APPARATUS FOR MEASURING EXCHANGE STIFFNESS AT A PATTERNED DEVICE LEVEL

CROSS-REFERENCE TO RELATED APPLICATIONS

This application claims the benefit of provisional Patent Application Ser. No. 62/447,525, filed Jan. 18, 2017, entitled METHOD FOR MEASURING EXCHANGE COUPLING STRENGTH, assigned to the assignee of the present application, and incorporated herein by reference.

BACKGROUND OF THE INVENTION

Magnetic memories, particularly magnetic random access memories (MRAMs), have drawn increasing interest due to their potential for high read/write speed, excellent endurance, non-volatility and low power consumption during operation. An MRAM can store information utilizing magnetic materials as an information recording medium. One type of MRAM is a spin transfer torque random access memory (STT-MRAM). STT-MRAM utilizes magnetic junctions written at least in part by a current driven through the magnetic junction. For example, a STT-MRAM may use conventional magnetic junctions having a pinned layer, a free layer and a nonmagnetic spacer layer between the pinned and free layers. The magnetization of the pinned layer is fixed, or pinned, in a particular direction. The free layer has a changeable magnetization. The nonmagnetic spacer layer may be a conductor or a tunneling barrier layer. A spin polarized current driven through the magnetic junction exerts a spin torque on the magnetic moment of the free layer. As a result, magnetic moment of the free layer may be switched to a desired state. Thus, information may be written to the magnetic junction. The data are read based on the magnetic junction's magnetoresistance, which depends upon the relative orientation of the free layer magnetic moment and the pinned layer magnetic moment.

Because of their potential for use in a variety of applications, research in magnetic memories is ongoing. Mechanisms for improving the performance of STT-MRAM and other thin film magnetic memories are desired. The parameters that affect the performance of the magnetic junctions are, therefore, desired to be understood. Accordingly, what is needed is a method and system that may improve the characterization of magnetic memories. The method and system described herein address such a need.

BRIEF SUMMARY OF THE INVENTION

A method and apparatus determine an exchange stiffness of a free layer residing in a magnetic junction. The method includes performing spin torque ferromagnetic resonance measurements for the magnetic junction. The spin torque ferromagnetic resonance measurements indicate characteristic frequencies corresponding to spin wave modes in the free layer. The method also includes calculating the exchange stiffness of the free layer based upon the plurality of characteristic frequencies. In some embodiments, the magnetic junction has an aspect ratio greater than 1.5 and less than ten. In some embodiments, the magnetic junction resides on a wafer including other magnetic junctions for a device. The other magnetic junctions may be arranged as in a magnetic memory. The magnetic junction undergoing spin torque ferromagnetic resonance has a different aspect ratio than the magnetic junctions usable in the device.

BRIEF DESCRIPTION OF SEVERAL VIEWS OF THE DRAWINGS

FIGS. 5A-5E depict another exemplary embodiment of a magnetic junction indicating the nodes in various modes of spin waves that may be excited in spin torque ferromagnetic resonance.

DETAILED DESCRIPTION OF THE INVENTION

Figure 1:
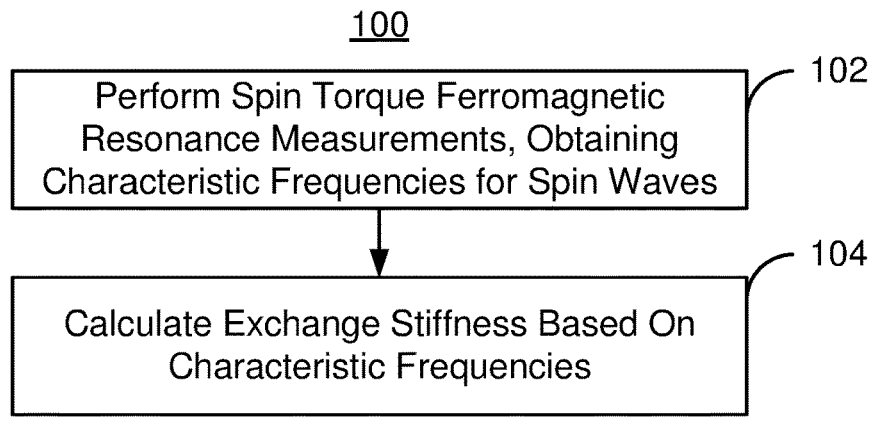
FIG. 1 is a flow chart depicting an exemplary embodiment of a method for determining the exchange stiffness for a magnetic junction using spin torque ferromagnetic resonance.

The exemplary embodiments relate to characterization of magnetic junctions usable in magnetic devices, such as magnetic memories, and the devices using such magnetic junctions. The magnetic junctions may be programmable using spin transfer torque. The magnetic memories may include spin transfer torque magnetic random access memories (STT-MRAMs) and may be used in electronic devices employing nonvolatile memory. Such electronic devices include but are not limited to cellular phones, smart phones, tables, laptops and other portable and non-portable computing devices. The following description is presented to enable one of ordinary skill in the art to make and use the invention and is provided in the context of a patent application and its requirements. Various modifications to the exemplary embodiments and the generic principles and features described herein will be readily apparent. The exemplary embodiments are mainly described in terms of particular methods, systems and implementations. However, the methods and systems will operate effectively in other implementations. Phrases such as "exemplary embodiment", "one embodiment" and "another embodiment" may refer to the same or different embodiments as well as to multiple embodiments. The embodiments will be described with respect to systems and/or devices having certain components. However, the systems and/or devices may include more or less components than those shown, and variations in the arrangement and type of the components may be made without departing from the scope of the invention. The exemplary embodiments will also be described in the context of particular methods having certain steps. However, the method and system operate effectively for other methods having different and/or additional steps and steps in different orders that are not inconsistent with the exemplary embodiments. Thus, the present invention is not intended to be limited to the embodiments shown, but is to be accorded the widest scope consistent with the principles and features described herein.

A method and apparatus determine an exchange stiffness of a free layer residing in a magnetic junction. The method includes performing spin torque ferromagnetic resonance (ST-FMR) measurements for the magnetic junction. The spin torque ferromagnetic resonance measurements indicate characteristic frequencies corresponding to fundamental (quasi-uniform) and spin wave modes in the free layer. The method also includes calculating the exchange stiffness of the free layer based upon the plurality of characteristic frequencies. In some embodiments, the magnetic junction has an aspect ratio greater than 1.5 and less than ten. In some embodiments, the magnetic junction resides on a wafer including other magnetic junctions for a device. The other magnetic junctions may be arranged as in a magnetic memory. The magnetic junction undergoing ST-FMR has a different aspect ratio than the magnetic junctions usable in the device.

The exemplary embodiments are described in the context of particular methods, magnetic junctions and magnetic devices having certain components. One of ordinary skill in the art will readily recognize that the present invention is consistent with the use of magnetic junctions and magnetic memories having other and/or additional components and/or other features not inconsistent with the present invention. The method and system are also described in the context of current understanding of the spin transfer phenomenon, of magnetic anisotropy, exchange stiffness and other physical phenomenon. Consequently, one of ordinary skill in the art will readily recognize that theoretical explanations of the method and system are made based upon this current understanding. However, the method and system described herein are not dependent upon a particular physical explanation. The method and system are described in the context of magnetic junctions and/or substructures having particular layers. However, one of ordinary skill in the art will readily recognize that magnetic junctions and/or substructures having additional and/or different layers not inconsistent with the method and system could also be used. Moreover, certain components are described as being magnetic, ferromagnetic, and ferrimagnetic. As used herein, the term magnetic could include ferromagnetic, ferrimagnetic or like structures. Thus, as used herein, the term "magnetic" or "ferromagnetic" includes, but is not limited to ferromagnets and ferrimagnets. As used herein, "in-plane" is substantially within or parallel to the plane of one or more of the layers of a magnetic junction. Conversely, "perpendicular" and "perpendicular-to-plane" corresponds to a direction that is substantially perpendicular to one or more of the layers of the magnetic junction.

As discussed above, in continuing to develop magnetic junctions for magnetic devices, such as STT-MRAM, characteristics of the magnetic junctions are desired to be investigated. One such characteristic is the exchange stiffness ($A_{ex}$). The exchange stiffness is a measure of the magnetic coupling within a particular layer and affects the performance of the magnetic junction. An exchange stiffness that is less than infinite results in increased energy required to switch the state of a free layer using spin transfer torque. This is because a finite exchange stiffness allows for the excitation of modes other than the fundamental mode, in which all moments move coherently. The excitation of other modes results in the heat dissipation and an attendant increase in the current and voltage required to write to the magnetic junction. Exchange stiffness of a magnetic junction programmed via STT may, therefore, be desired to be known.

The exchange stiffness of a material may be measured in some cases. Exchange stiffness measurements for bulk samples and thicker films, for example of at least ten nanometers thick, may be made using techniques such Brillouin light scattering and conventional spin-wave FMR. However, the free layer of a magnetic junction in STT-MRAM is typically less than fifty nanometers thick. In some cases, the free layer of a magnetic junction is less than two nanometers thick. The above techniques for measuring exchange stiffness may be inappropriate for use in connection with the thin free layer. Because of the presence of interfaces, grains and other growth-related morphology of a thin free layer, the exchange stiffness of the thin free layer is expected to be less than that of a bulk sample or thicker films of the same materials. The bulk and/or thick layer measurements of the exchange stiffness may not be used in place of the exchange stiffness of thin free layers. As such, another mechanism for characterizing the exchange stiffness of a free layer in a magnetic junction is desired.

FIG. 1 is a flow chart depicting an exemplary embodiment of a method 100 for determining the exchange stiffness using spin torque ferromagnetic resonance (FMR). Spin torque FMR may also be termed spin transfer FMR. Consequently, STT-FMR is used herein to refer to either/both. For simplicity, some steps may be omitted, performed in another order, include substeps and/or combined. The method 100 is used in conjunction with magnetic junctions that may be usable in a magnetic devices such as a STT-MRAM and, therefore, in a variety of electronic devices.

Figure 2A:
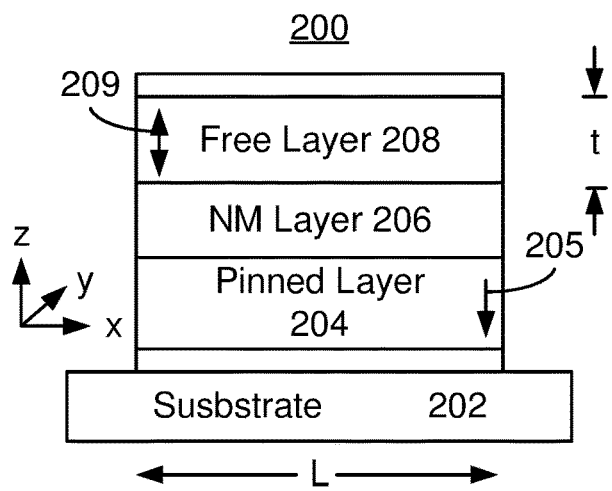
FIGS. 2A-2B depict an exemplary embodiment of a magnetic junction usable in a magnetic devices such as a magnetic memory programmable using spin transfer torque.
Figure 2B:
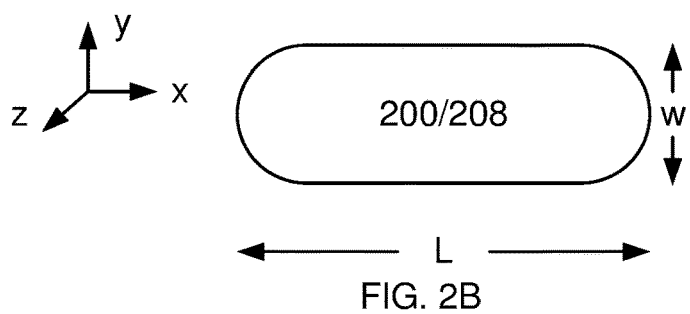

FIGS. 2A-2B depict an exemplary embodiment of a magnetic junction 200 with which the method 100 may be used. FIGS. 2A-2B are not to scale and only structures of interest are separately labeled and included. Referring to FIGS. 1-2B, the method 100 is described in the context of the magnetic junction 200. However, the method 100 may be used in connection with other magnetic junction(s). Further, the method 100 is described as performing measurements of a single magnetic junction. In some embodiments, the method 100 may be performed for multiple magnetic junctions substantially simultaneously. The magnetic junction 200 resides on a substrate 202 and includes at least a pinned layer 204, a nonmagnetic spacer layer 206 and a free layer 208. In the embodiment shown, the magnetic junction 200 is a bottom pinned magnetic junction (pinned layer 204 closer to the substrate than the free layer 208). However, nothing prevents the use of a top pinned magnetic junction (free layer 208 closer to the substrate 202 than the pinned layer 204), a dual magnetic junction (including an additional nonmagnetic spacer layer and an additional pinned layer) or other analogous magnetic junction. The free layer 208 and pinned layer 204 may be single layers or multilayers. The nonmagnetic spacer layer 206 may be a conductive layer or an insulating tunneling barrier layer such as crystalline MgO. In the embodiment shown, the magnetic layers 204 and 208 may have a high perpendicular magnetic anisotropy (PMA). Stated differently, the perpendicular magnetic anisotropy energy may exceed the out-of-plane demagnetization energy for the pinned layer 204 and the free layer 208. Thus, the pinned layer magnetic moment 205 and free layer magnetic moment 209 are stable perpendicular-to-plane. The free layer magnetic moment 209 is stable in the +z direction or the −z direction. In other embodiments, the magnetic moments 205 and 209 may be stable in other directions. The magnetic junction 200 has an in-plane aspect ratio of L/w (length divided by width) shown in FIG. 2B. As can be seen in FIG. 2A, the free layer 208 has a thickness t. In general, the free layer 208 is relatively thin. For example, t may be not more than five nanometers. In general, the free layer thickness t is four nanometers or less. In some embodiments the free layer 208 is less than two nanometers thick.

Referring to FIGS. 1-2B, ST-FMR measurements are performed for the magnetic junction 200, via step 102. In order to perform FMR measurements, the free layer magnetic moment 209 is excited so that it precesses around its stable state at characteristic frequencies. In ST-FMR, the free layer magnetic moment 209 is excited using a spin polarized current driven through the magnetic junction 200, generally in the current perpendicular-to-plane (CPP) direction. The current may be spin polarized due to the pinned layer magnetic moment 205. This spin polarized current exerts a torque on the free layer magnetic moment 209, inducing precession. In some embodiments, the spin polarized current used is an alternating current having a frequency in the GHz range.

In order for the torque from the spin polarized current to more readily act on the free layer 208, an additional magnetic field may be applied along, or at a nonzero angle to the z-axis as part of the ST-FMR measurement. However, other directions may be used. In some embodiments, the magnetic field may have a large DC (constant) component and a small modulating component. The DC field component is typically applied along the direction normal to the sample surface (i.e. along the z-axis). However, nothing prevents the DC component from being applied in another direction. The modulating component may be an alternating magnetic field having a frequency no more than one tenth that of the spin polarized current. In some such embodiments, the alternating magnetic field has a frequency of not more than one hundredth of the spin polarized current. For example, the modulation field may be in the kHz range. The modulating component may be applied in any direction, but is generally parallel to the DC component. In other embodiments, the magnetic field applied may be constant/unmodulated.

The ST-FMR measurements result in data indicating characteristic frequencies corresponding to standing spin wave modes in the free layer 208. In general, standing spin wave modes of the magnetic junction depend upon the exchange stiffness and the perpendicular magnetic anisotropy of the free layer 208. The applied magnetic field (if any), the magnetic field due to the pinned layer 204 as well as the length and width of the free layer 208 also affect the frequencies of the spin wave normal modes. The precession of the magnetic moment 209 may have resonances at the characteristic frequencies for stable modes for standing spin waves for the free layer 208. These characteristic frequencies can be detected by measuring the voltage across, resistance of, or power through the magnetic junction 200 while the spin polarized current is driven through the magnetic junction 200. Peaks in these quantities occur at these characteristic frequencies for the spin waves. For example, a voltage versus field or frequency spectrum includes resonant peaks corresponding to the characteristic frequencies.

Use of the large aspect ratio magnetic junction 200 may allow for a simpler standing spin wave mode structure for the ST-FMR measurements performed in step 102. This is in contrast to the complex mode structure generally present for magnetic junctions used in STT-MRAM. These magnetic junctions (not shown) have an aspect ratio of approximately one and a substantially circular footprint. These magnetic junctions are susceptible to breaking of circular symmetry by small changes in geometry and splitting of modes. In contrast, the mode structure for the large aspect ratio magnetic junction 200 may be less ambiguous, less likely to result in degenerate modes and more amenable to investigation via STT-FMR. As a result, the data provided by step 104 may be more easily and better analyzed. However, in alternate embodiments, magnetic junctions having other shapes and other aspect ratios, including smaller aspect ratios, might be employed.

The exchange stiffness of the free layer 208, and thus of the magnetic junction 200, is calculated based upon the characteristic frequencies of the spin waves, via step 104. Thus, the characteristic frequencies for spin waves in the free layer 208 are determined from the STT-FMR data obtained in step 102. These characteristic frequencies are then used to determine the exchange stiffness. Determination of the exchange stiffness from the characteristic frequency in step 104 may be carried out using numerical simulation, a micromagnetic model, analytical model, a quasi-numerical model, another model or some combination thereof. These models employ boundary conditions for the edges of the free layer and other limitations or assumptions. For example, one analytical model treats standing spin waves in the magnetic junction 200 in a manner similar to a standing physical waves on a string. For such a model, the spacing between characteristic frequencies is proportional to the exchange stiffness and the difference between the squares of the mode numbers. The data from ST-FMR measurements may be fit to this model and/or other models. The exchange stiffness may be taken from the best fit for the data.

Using the method 100, the exchange stiffness of the thin free layer 208 may be measured despite the small thickness of the free layer 208. This exchange stiffness may be used in determining switching characteristics and other attributes of magnetic junctions employing a similar free layer. For example, the free layer 208 may be fabricated at the same time as free layers for other magnetic junctions (not shown) on the same substrate 202. These other magnetic junctions may have a different aspect ratio and may be used in a magnetic device such as STT-MRAM. The free layers of such magnetic junctions have substantially the same thickness and stoichiometry as the free layer 208. The exchange stiffness measured for the free layer 208 may be used for the free layers of such magnetic junctions. As a result, the magnetic characteristics of magnetic junctions may be better empirically determined.

Figure 3:
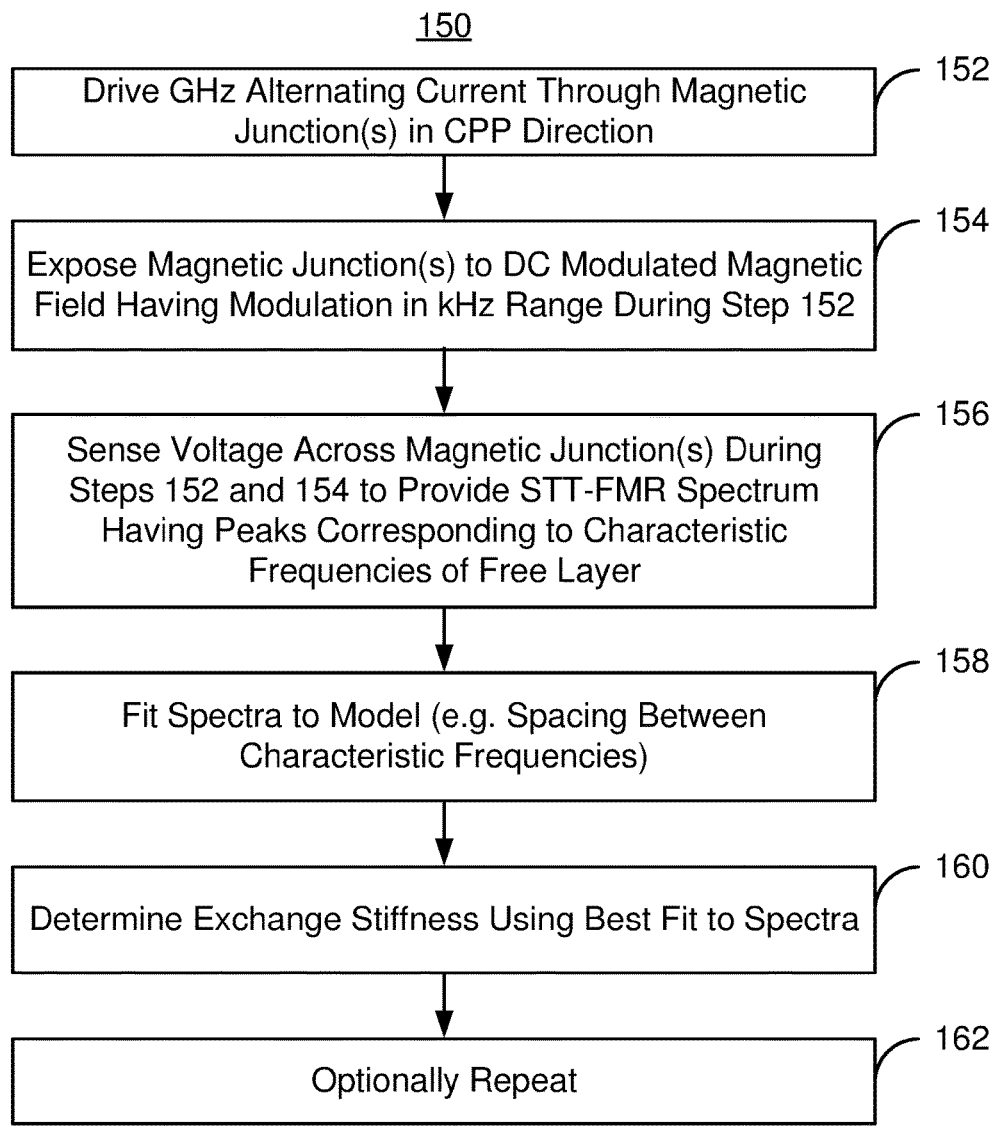
FIG. 3 is a flow chart depicting another exemplary embodiment of a method for determining the exchange stiffness for a magnetic junction using spin torque ferromagnetic resonance.
Figure 4:
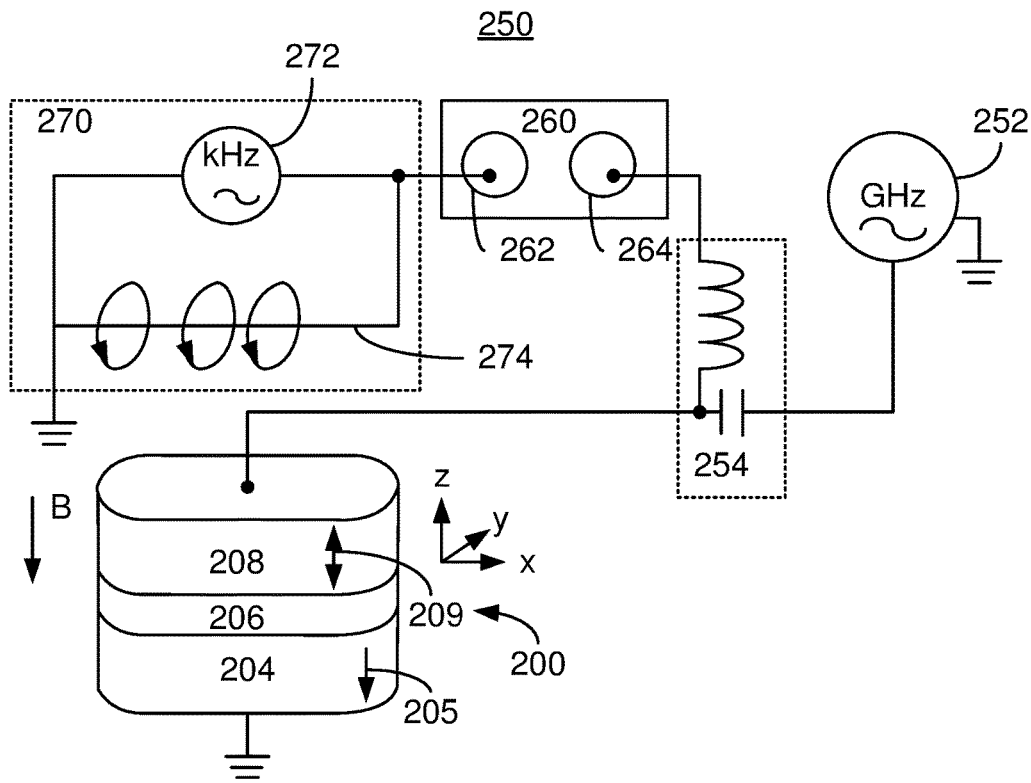
FIG. 4 depicts an exemplary embodiment of a system for determining the exchange stiffness for a magnetic junction using spin torque ferromagnetic resonance.

FIG. 3 is a flow chart depicting an exemplary embodiment of a method 150 for determining the exchange stiffness of a thin free layer using ST-FMR. For simplicity, some steps may be omitted, performed in another order, include substeps and/or combined. The method 150 is used in conjunction with magnetic junctions that may be usable in a magnetic devices such as a STT-MRAM and, therefore, in a variety of electronic devices. The method 150 is also described in conjunction with the magnetic junction 200. FIG. 4 depicts an exemplary embodiment of a system 250 for determining the exchange stiffness for a magnetic junction 200 using ST-FMR. The method 150 is described in connection with the system 250. The system 250 includes a current source 252, a bias circuit 254, lock-in amplifier 260 and magnetic field generation block 270. Also shown in FIG. 4 is the magnetic junction 200 under investigation. Although one magnetic junction 200 is shown and described for the method 150 and system 250, the method 150 and system 250 may be extended to investigate multiple magnetic junctions in parallel.

Referring to FIGS. 3-4, an alternating current is driven through the magnetic junction 200, via step 152. Thus, the current source 252 drives an alternating current through the magnetic junction 200. In the embodiment shown, the frequency of the alternating current is in the GHz regime.

Via step 154, the magnetic junction 200 is exposed to a DC modulated magnetic field while the current is driven through the magnetic junction 200. The magnetic field, B, is generally applied along the z-axis as shown in FIG. 4. However, another direction may be used. The magnetic field is generated by the magnetic field generation block 270. For example, a line 274 through which current is driven may be in proximity to the magnetic junction 200. The magnetic field from this line 274 acts upon the magnetic junction 200. In the embodiment shown, the magnetic field has both a constant, DC component and a time varying modulation component. As discussed above, the modulation component may be parallel to the DC component or may be at an arbitrary angle from the DC component. The DC component has a magnitude significantly larger than the modulation component. The modulation component provided by current generator 272 may have a frequency significantly less than that of the spin polarized current driven through the magnetic junction 200 in step 152. For example, the modulation component of the magnetic field may be in the kHz regime. The frequencies selected for the current generators 252 and 272 may depend upon the expected resonance due to precession of the free layer magnetic moment 209 and the frequency desired for lock-in detection, respectively.

Figure 5D:
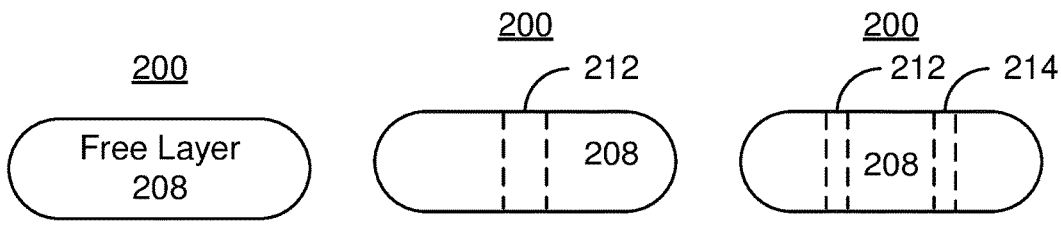
Figure 5D:
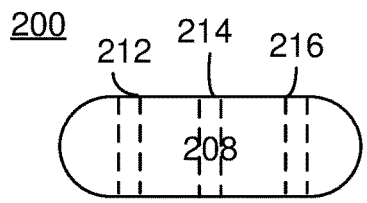
Figure 5E:
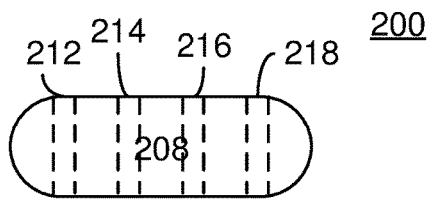

FIGS. 5A-5E depict the magnetic junction 200 in which various nodes for standing spin wave modes are indicated. The modes shown in FIGS. 5A-5E may be present when free layer magnetic moment 209 is excited via steps 152 and 154. It is assumed for FIGS. 5A-5E that the standing spin waves in the magnetic junction 200 are similar to a physical waves on a string. The wavelength, $\lambda$, of a particular mode is given by $\lambda=2L/n$, where n is the mode number. Thus, the lowest order mode (n=1) has a wavelength that is twice the length of the free layer 208. This is the mode shown in FIG. 5A. In such a mode, the spins precess coherently. FIG. 5B depicts the second mode having a wavelength equal to the length, L (not labeled in FIGS. 5A-5E) of the magnetic junction 200. Consequently, this mode has a single node 212 and n=2. FIG. 5C depicts the magnetic junction 200 for the next mode (n=3), having two nodes 212 and 214. FIG. 5D depicts the magnetic junction 200 for the fourth mode (n=4) in which there are three nodes 212, 214 and 216. FIG. 5E depicts the magnetic junction 200 for the fifth mode in which there are four nodes 212, 214, 216 and 218. Because of the large aspect ratio of the magnetic junction 200, the mode structure for at least the spin wave modes shown in FIGS. 5A, 5B, 5C and 5D is relatively simple. In some cases, this mode structure breaks down for the fifth mode shown in FIG. 5E. However, the relatively simple mode structure for the magnetic junction 200 may simplify analysis of the data obtained via steps 152, 154 and 156 of the method 150.

The ST-FMR rectified voltage (ST-FMR is a self-rectifying technique and is sometimes referred to as the spin-torque diode effect) across the magnetic junction 200 is sensed while the magnetic field and spin polarized current are provided, via step 156. In the embodiment shown, this is accomplished using the lock-in amplifier 260. The signal from the magnetic field generation block 270 is provided to the lock-in amplifier 260 as a reference signal via port 262. The voltage across the magnetic junction 200 is provided via bias circuit 254 as a signal via port 264. Thus, the ST-FMR data may be acquired via step 152, 154 and 156.

Figure 6:
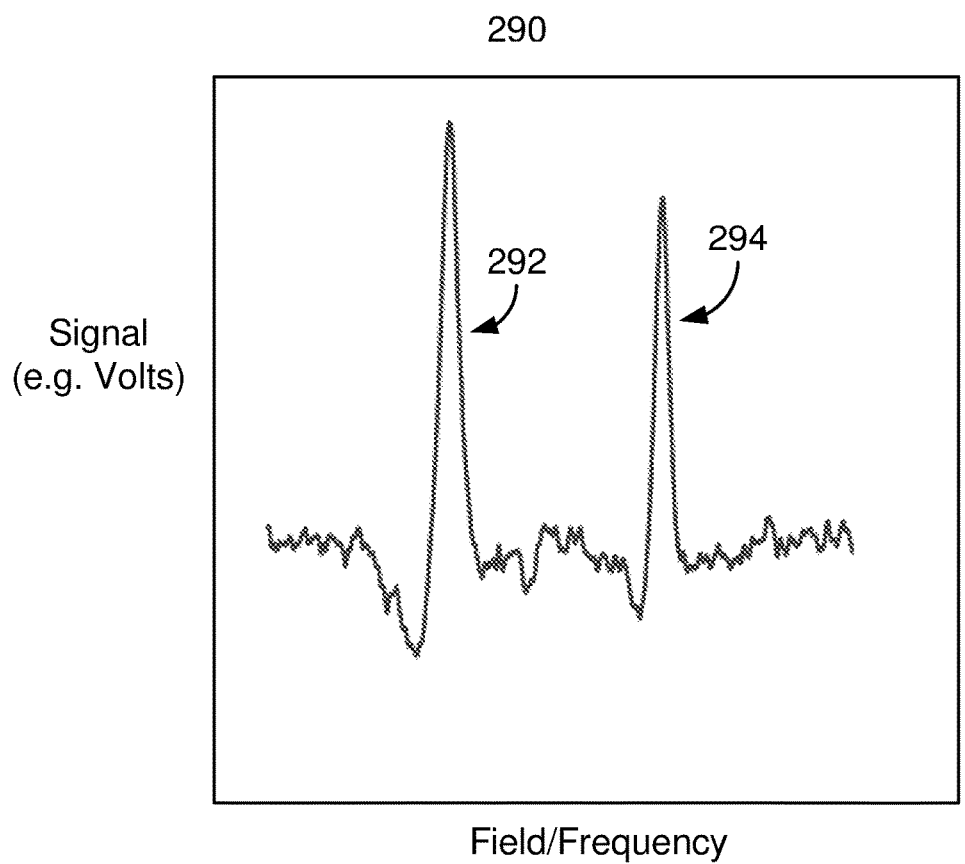
FIG. 6 depicts an exemplary embodiment of a spectrum provided using spin torque ferromagnetic resonance.

FIG. 6 depicts an exemplary embodiment of a spectrum 290 provided using ST-FMR from the method 150 and system 250. More specifically, FIG. 6 is a representation of the data that may be obtained in step 156. The spectrum 290 may be only a portion of the data obtained in step 156. Further, the spectrum 290 is for explanatory purposes only and not intended to represent a particular magnetic junction 200, system 250 or method 150. The spectrum 290 depicts the signal from the lock-in amplifier 260 as a function of applied field or frequency. In some embodiments, the signal obtained versus field is directly proportional to the signal obtained for particular frequencies. The spectrum includes two peaks 292 and 294 that correspond to two different spin wave standing modes for the magnetic junction 200. Thus, each peak 292 and 294 has a characteristic frequency. The characteristic frequency of each peak 292 and 294 and separation in frequency between peaks 292 and 294 can be determined from the spectrum 290.

The data, such as the spectrum 290, are fit to the desired model(s), via step 158. For example, one analytical model treats standing spin waves in the magnetic junction 200 in a manner similar to a physical waves on a string. In such an embodiment, the wavelength, $\lambda$, of a particular mode is given by $\lambda=2L/n$, where n is the mode number. Thus, the lowest order mode (n=1) has a wavelength that is twice the length of the free layer 208. The angular frequency, $\omega$, for a mode of such a model is given by $\omega=\omega_0+A_{ex}n^2/L^2$, where $A_{ex}$ is the exchange stiffness of the free layer 208 and n is the mode number. Using this model, the separation between the peaks 292 and 294 in the spectrum 290, as well as other peaks that are not shown in FIG. 6, can be fit to the above equation.

The exchange stiffness of the free layer 208 is determined based on the best fit to the data, via step 160. In some embodiments, this includes adjusting the exchange stiffness in one or more of numerical simulation(s), micromagnetic model(s), analytical model(s) such as the string discussed above, a quasi-numerical model(s), other model(s) or some combination thereof. The exchange stiffness may be taken from the best fit for the data.

Steps 152, 154, 156, 158 and 160 may optionally be repeated for the same sample or other sample(s), via step 162. As a result, sufficient data to have confidence in the resulting exchange stiffness may be obtained.

Using the method 150, the exchange stiffness of the thin free layer 208 may be measured despite the small thickness of the free layer 208. Thus, the behavior of magnetic junctions employing thin free layers may be better predicted.

Figure 7:
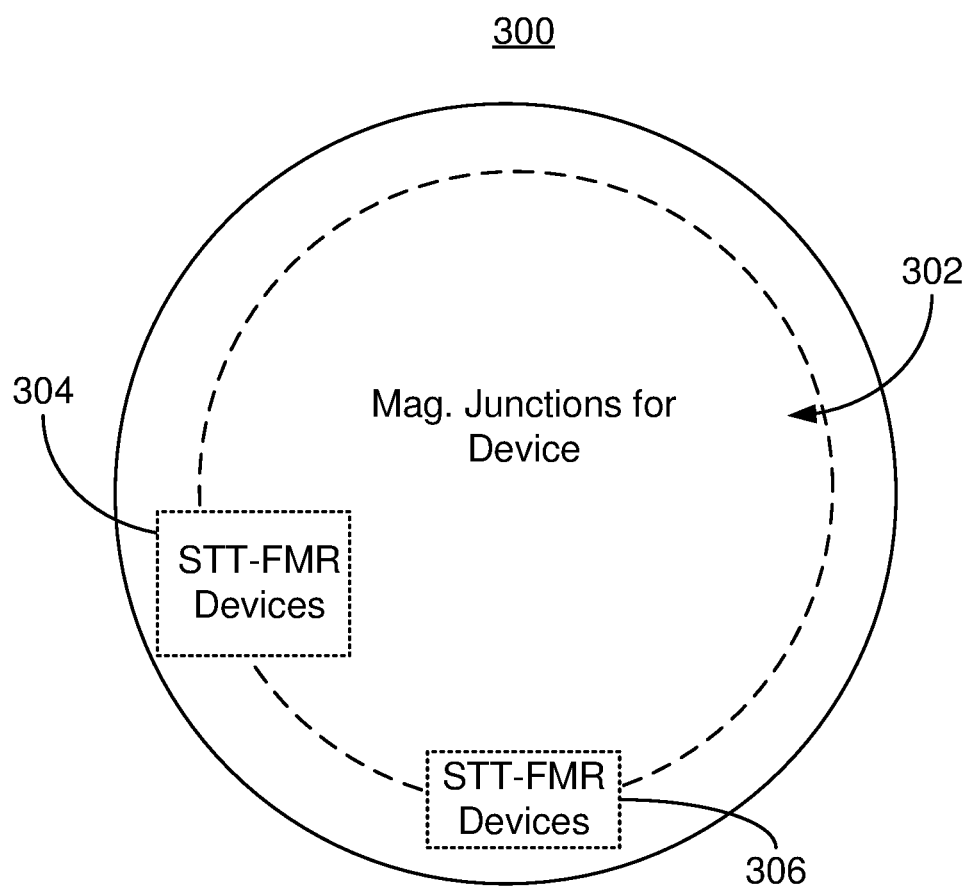
FIG. 7 depicts an exemplary embodiment of a substrate including magnetic junctions usable in the device and magnetic junctions for determining the exchange stiffness using spin transfer torque ferromagnetic resonance.

FIG. 7 depicts an exemplary embodiment of a wafer 300 including magnetic junctions usable in magnetic devices and magnetic junctions for determining the exchange stiffness using ST-FMR. The wafer 300 may thus make particular use of the method(s) 100 and/or 150 and the system 250. The wafer includes region 302 in which magnetic junctions usable in device are formed. For example, the region 302 may include magnetic junctions usable in STT-MRAM or another device. The wafer 300 also includes regions 304 and 306 that includes magnetic junctions such as the magnetic junction 200, which are configured to have their exchange stiffness measured using the method 100 and/or 150. In the embodiment shown, the regions 304 and 306 are segregated from the region 302. Thus, magnetic junctions for which exchange stiffness may be more readily measured are grouped together near the edges of the wafer 300. In other embodiments, the magnetic junctions corresponding to the regions 304 and 306 may be located in other areas. For example, such magnetic junctions may be distributed throughout the wafer 300 or grouped together at different location(s).

The layers for the magnetic junctions in the regions 302, 304 and 306 may be deposited together. The materials used for the layers, including the free layer, may be the same or the junctions in the regions 304 and 306 as for the region 302. Similarly, the thicknesses of the free layers for magnetic junctions in the regions 302, 304 and 306 may be the same. Because they are all on the same wafer 300, the magnetic junctions for the regions 302, 304 and 306 may all undergo the same heat treatments. However, the footprint of the magnetic junctions in the regions 304 and 306 may be different from the footprint of the magnetic junctions in region 302. In particular, the aspect ratio for the magnetic junctions in the regions 304 and 306 may be larger than the aspect ratio of the magnetic junctions in the region 302. In some embodiments, the aspect ratio for the magnetic junctions in region 302 may be near one, while the aspect ratio for magnetic junctions in the regions 304 and 306 may be greater than three.

The method(s) 100 and/or 150 may be used to determine the exchange stiffness for the magnetic junctions in the regions 304 and 306 and, therefore, for the magnetic junctions in the region 302. As a result, the exchange stiffness may be determined on an individual wafer-by-wafer basis.

Although the method and apparatus have been described in the context of specific features, steps and components, one of ordinary skill in the art will recognize that one or more of these features, steps and/or components may be combined in other manners not inconsistent with the description herein.

A method and system for determining the exchange stiffness for a magnetic junction having thin free layer(s) has been described. The method and system have been described in accordance with the exemplary embodiments shown, and one of ordinary skill in the art will readily recognize that there could be variations to the embodiments, and any variations would be within the spirit and scope of the method and system. Accordingly, many modifications may be made by one of ordinary skill in the art without departing from the spirit and scope of the appended claims.

We claim:

1. A method for determining an exchange stiffness of a free layer residing in a magnetic junction, the method comprising:
    performing a plurality of spin torque ferromagnetic resonance (ST-FMR) measurements for the magnetic junction, the plurality of ST-FMR measurements indicating a plurality of characteristic frequencies corresponding to a plurality of spin wave modes in the free layer, the free layer having an aspect ratio of at least 1.5 and not more than ten, the step of performing the plurality of ST-FMR measurements including
        driving an alternating current through the magnetic junction; and
        calculating the exchange stiffness of the free layer based upon the plurality of characteristic frequencies, the calculating the exchange stiffness further including
            determining the exchange stiffness using at least one frequency spacing between the plurality of characteristic frequencies, the determining the exchange stiffness further including;
                fitting the at least one frequency spacing to at least one of a numerical model, an analytical model and a quasi-numerical model; and
                selecting the exchange stiffness from a best fit of the at least one of the numerical model, the analytical model and the quasi-numerical model.

2. The method of claim 1 wherein the aspect ratio is not more than eight.

3. The method of claim 1 wherein the aspect ratio is greater than three.

4. The method of claim 1 wherein the free layer has a free layer thickness and at least one material, wherein the magnetic junction resides on a wafer including a plurality of magnetic junctions, each of the plurality of magnetic junctions having an additional aspect ratio different from the aspect ratio and having an additional free layer, the additional free layer having an additional free layer thickness and at least additional material substantially the same as the free layer thickness and the at least one material.

5. The method of claim 4 wherein the additional aspect ratio is less than the aspect ratio.

6. The method of claim 4 wherein the plurality of magnetic junctions are part of a magnetic random access memory.

7. The method of claim 1 wherein the alternating current has a frequency of at least one GHz and wherein the step of performing the plurality of ST-FMR measurements further includes:
    exposing the magnetic junction to a magnetic field at an angle from a free layer magnetic moment during the step of driving the alternating current; and
    sensing a rectified voltage across the magnetic junction, the rectified voltage providing the plurality of characteristic frequencies.

8. The method of claim 7 wherein the magnetic field is modulated at a magnetic frequency not more than one tenth of the current frequency.

9. A method for determining an exchange stiffness of a free layer residing in a magnetic junction, the method comprising:
    performing a plurality of spin torque ferromagnetic resonance (ST-FMR) measurements for the magnetic junction, the free layer having an in-plane aspect ratio of at least 3.5 and not more than 4.5, the plurality of ST-FMR measurements indicating a plurality of characteristic frequencies corresponding to a plurality of spin wave modes in the free layer, the step of performing the plurality of ST-FMR measurements further including
        driving an alternating current through the magnetic junction, the alternating current having a current frequency of at least one GHz;
        exposing the magnetic junction to a magnetic field at an angle from a free layer magnetic moment during the step of driving the alternating current, the magnetic field having a constant component with a first magnitude and a modulation component, the modulation component having a second magnitude and varying at a magnetic field frequency of not more than one hundredth of the current frequency, the second magnitude being less than the first magnitude; and
        sensing a rectified voltage across the magnetic junction, the voltage providing the plurality of characteristic frequencies;
    calculating the exchange stiffness of the free layer based upon at least one frequency spacing between the plurality of characteristic frequencies, the step of calculating the exchange stiffness including
        fitting the at least one frequency spacing to a model; and selecting the exchange stiffness from a best fit of the model.

10. The method of claim 9 wherein the free layer has a free layer thickness and at least one material, wherein the magnetic junction resides on a wafer including a plurality of magnetic junctions, each of the plurality of magnetic junctions having an additional aspect ratio different from the aspect ratio and having an additional free layer, the additional free layer having an additional free layer thickness and at least additional material substantially the same as the free layer thickness and the at least one material.

\* \* \* \* \*